United States Patent
Sanchez Calvo et al.

(10) Patent No.: US 8,475,040 B2
(45) Date of Patent: Jul. 2, 2013

(54) X-RAY APPARATUS FOR TOMOSYNTHESIS

(75) Inventors: David Sanchez Calvo, Algete (ES); Ildefonos Moreno Vallejo, Algete (ES)

(73) Assignee: Socledad Española de Electromedicina y Calidad, S.A., Algete (ES)

( * ) Notice: Subject to any disclaimer, the term of this patent is extended or adjusted under 35 U.S.C. 154(b) by 281 days.

(21) Appl. No.: 12/996,744

(22) PCT Filed: Mar. 4, 2009

(86) PCT No.: PCT/ES2009/070054
§ 371 (c)(1),
(2), (4) Date: Feb. 10, 2011

(87) PCT Pub. No.: WO2010/100292
PCT Pub. Date: Sep. 10, 2010

(65) Prior Publication Data
US 2011/0135055 A1   Jun. 9, 2011

(51) Int. Cl.
*H05G 1/02* (2006.01)
(52) U.S. Cl.
USPC .......................................................... 378/196
(58) Field of Classification Search
USPC .......................................... 378/196, 197, 198
See application file for complete search history.

(56) References Cited

U.S. PATENT DOCUMENTS

| | | | |
|---|---|---|---|
| 2002/0080921 A1* | 6/2002 | Smith et al. | 378/189 |
| 2004/0052334 A1* | 3/2004 | Pillai et al. | 378/196 |
| 2005/0234327 A1 | 10/2005 | Saracen | |
| 2008/0240343 A1 | 10/2008 | Jabri | |

FOREIGN PATENT DOCUMENTS

| | | | |
|---|---|---|---|
| FR | 2821263 A1 * | 8/2002 | |
| WO | 03021629 | 3/2003 | |

* cited by examiner

*Primary Examiner* — Glen Kao
(74) *Attorney, Agent, or Firm* — Dickinson Wright PLLC

(57) ABSTRACT

X-ray apparatus that allows performing tomosynthesis as well as lateral thoracic radiographs from the stretcher itself, for which is comprises a fixed column and a revolving base that can move vertically along the fixed column, as well as rotate. Associated to this revolving base is a folding board and a support base for an arm of the x-ray tube and collimator assembly, with the specific property that the x-ray tube arm can turn independently of the detector, and the rotation of the revolving base is performed about an axis adjoining one of the sides of the fixed column, so that when the assembly is rotated it is possible to perform lateral thoracic radiographs without having to move patients from the stretcher on which they have been brought.

3 Claims, 5 Drawing Sheets

X-RAY APPARATUS FOR TOMOSYNTHESIS

CROSS-REFERENCE TO RELATED APPLICATIONS

This application is a National Stage of International Application No. PCT/ES2009/070054, filed Mar. 4, 2009. The entire disclosure of each of the above applications is incorporated herein by reference.

OBJECT OF THE INVENTION

The object of the present invention is an X-ray apparatus that, among other properties, has the essential and distinctive characteristic of allowing to perform tomosynthesis. Tomosynthesis is a radiological technique that allows viewing objects in three dimensions and is closely related to computerised tomography.

The X-ray apparatus object of the invention is also provided with a folding board and revolving base so that, in addition to obtaining x-ray images with the patient placed on the board horizontally, it also allows obtaining frontal radiographs of the thorax with the patient in a vertical position.

The present invention is characterised by the special configuration and design of the elements that conform the object of the invention that allow performing tomosynthesis.

In addition, the present invention is also characterised by the possibility of obtaining lateral thorax radiographs of a patient lying on a stretcher without having to move the patient.

Therefore, the present invention lies in the field of x-ray apparatuses and more specifically, of those provided with a folding board mounted on a revolving base.

BACKGROUND OF THE INVENTION

The prior art include patent FR2821263 A1 for x-ray apparatuses. The constructive features of this apparatus include a folding board associated to a base that rotates about a fixed column.

This apparatus allows obtaining a large number of radiographs, both with the patient lying horizontally on the board and with the patient in a vertical position; for the latter, the revolving base assembly is turned 90° and the board is folded, so that the x-ray detector and tubes are opposite one another and it is possible to obtain thoracic radiographs with the patient in a vertical position.

However, this apparatus has several limitations. The first and most important limitation is that the supporting arm of the x-ray tube does not rotate independently of the revolving base, so that it is not possible to perform tomosynthesis radiological tests as rotating the x-ray arm would require rotating of the entire revolving base, and therefore also the receiver and the folding board.

On another hand, this apparatus also does not allow obtaining radiographs of patients on a stretcher. As can be seen in FIG. 5 of the French patent cited as prior art, when the revolving base has been turned and the board has been folded the detector is placed opposite the x-ray tube so that there is a space between them. In the middle of this space is the fixed column on which the folder has been folded, thereby preventing a stretcher from passing.

It is also known document WO03/021629 relative to a digital flat panel x-ray receptor positioning in a diagnostic radiology wherein the detector and revolving base equipment is separated from the X-ray tube equipment.

Therefore, the object of the present invention is to develop an x-ray apparatus that can perform tomosynthesis, and in addition and complementarily, that also allows performing lateral thoracic radiographs even with patients on the stretcher used to carry them to the x-ray room.

DESCRIPTION OF THE INVENTION

The object of the present invention is an x-ray apparatus that allows performing tomosynthesis, for which it has a fixed column for control and power supply on which a revolving base is disposed, wherein this revolving base is in turned connected to a folding board and a support plate for the arm of the x-ray tube and collimator assembly, and a detector.

This support plate can be attached to the revolving base, so that rotating the revolving base will rotate the entire assembly, this is, the folding board, the arm of the x-ray tube and collimator assembly and the detector.

If this support plate is not connected to the revolving base, the arm and detector assembly can move longitudinally along the revolving base, to the most convenient position.

The x-ray and collimator arm has the specific property that it can revolve independently with respect to the detector, which allows performing tomosynthesis. It is important to point out that the shaft of the arm of the x-ray tube and collimator assembly coincides with the surface of the detector, which is necessary to perform tomosynthesis.

On another hand, as it is possible to link the rotation of the revolving base with the rest of the elements, namely the arm of the x-ray tube and collimator assembly, folding board and detector, it is possible to place all these elements vertically to allow obtaining radiographs of the chest, cranium, hip, vertebral column etc. with the patient in a vertical position without having to lie down on the stretcher.

Also due to the arrangement of the rotation axis of the revolving base with respect to the fixed control and power supply column, when the revolving base turns and with it all the elements connected to it (arm of the x-ray tube and collimator assembly, folding board and detector) a space is left between the detector and the x-ray tube through which a stretcher can pass, without its longitudinal displacement being hindered by the fixed column for control and power supply.

This also allows performing lateral thoracic radiographs with the patient still on the stretcher. This is an important advantage, as it is difficult to move or lift some patients from the stretcher due to their condition and it is desirable to simplify the performance of lateral radiographs so that it is not necessary to inconvenience the patient.

DESCRIPTION OF THE DRAWINGS

To complete the description being made and in order to aid a better understanding of its characteristics, the present descriptive memory is accompanied by a set of drawings with figures where, for purposes of illustration only and in a non-limiting manner, the most significant details of the invention are represented.

PREFERRED EMBODIMENT OF THE INVENTION

A preferred embodiment of the invention disclosed herein is described below with reference to the figures.

Figure 1:
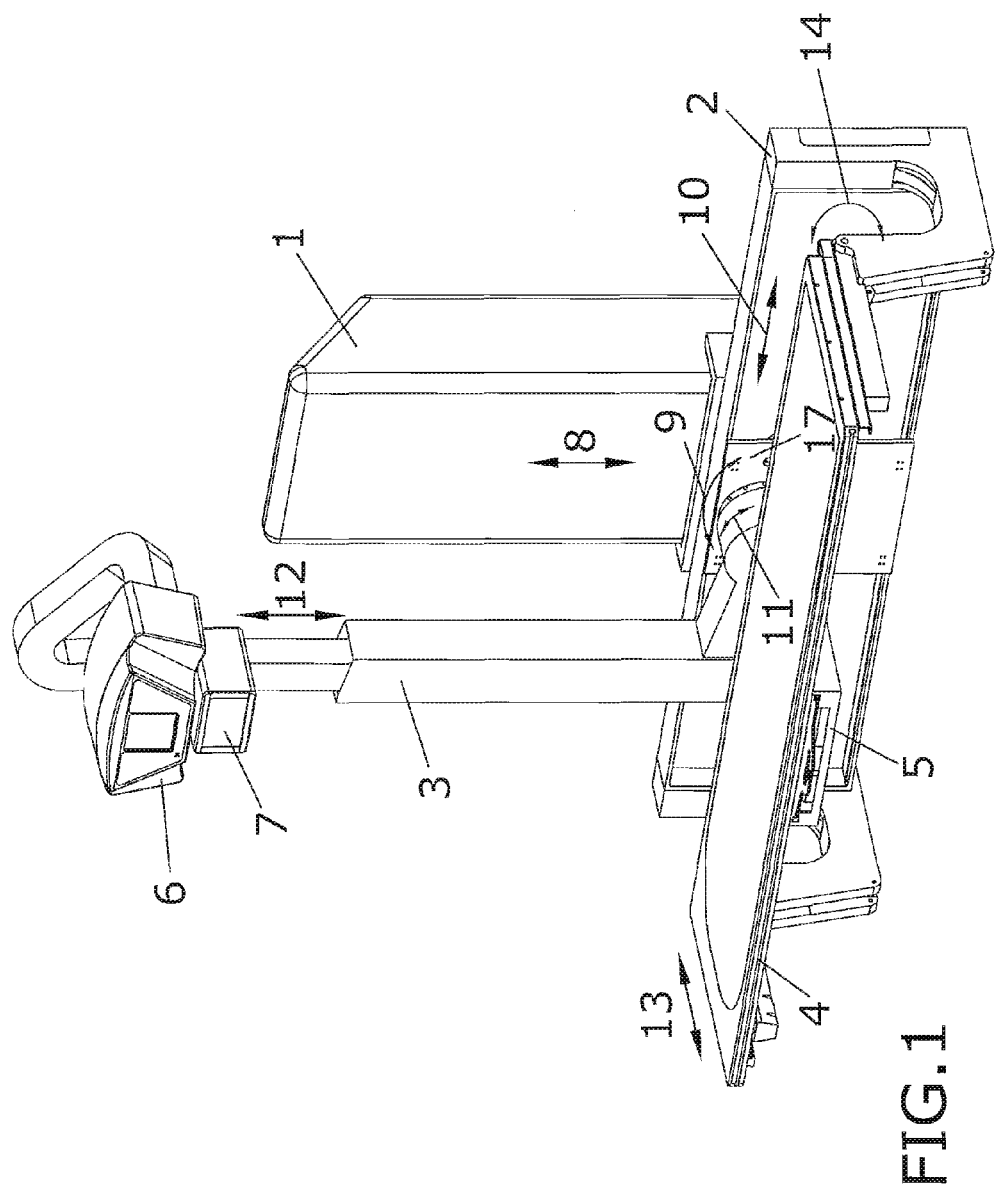
FIG. 1 shows a perspective view of the x-ray apparatus object of the invention, showing all of its component elements and the relationship between them.
Figure 2:
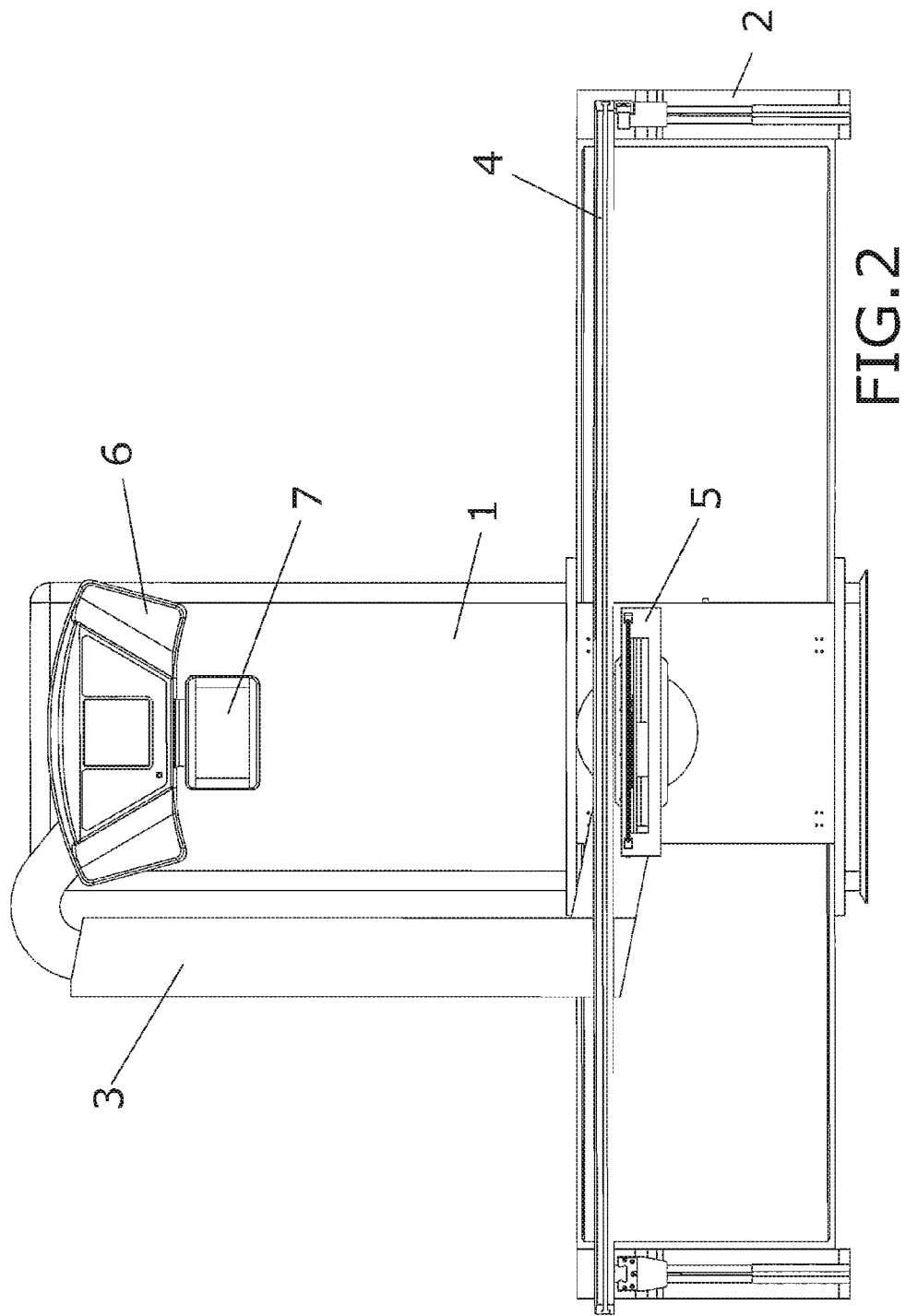
FIG. 2 shows a front view of the x-ray apparatus.

The x-ray apparatus object of the invention can be seen in FIG. 1, which shows that it comprises a fixed column (1) for control and power supply, associated to a revolving base (2).

The revolving base (2) is permanently attached to a folding board (4), so that the rotation of the revolving base (2) causes a rotation of said folding board (4).

Attached on the revolving base (2) is a support plate (17) on which are mounted a U-shaped arm (3) on the end of which are disposed the x-ray tube (6) and collimator (7) assembly and a detector (5).

This support plate (17) can be attached to the revolving base (2) such that the rotation of the revolving base (2) will turn all the elements, this is, the folding board (4), the support plate (17) and therefore the arm (3) of the x-ray tube (6) and collimator assembly and the detector (5).

In addition, this support plate (17) can be partially released from its attachment to the revolving base (2), so that it has a degree of freedom, and can move longitudinally along the length of the revolving plate (2) to the most convenient position.

The revolving base (2) assembly moves longitudinally (8) with respect to the fixed column (1) in a vertical sense, allowing to raise and lower the entire assembly.

Figure 5:
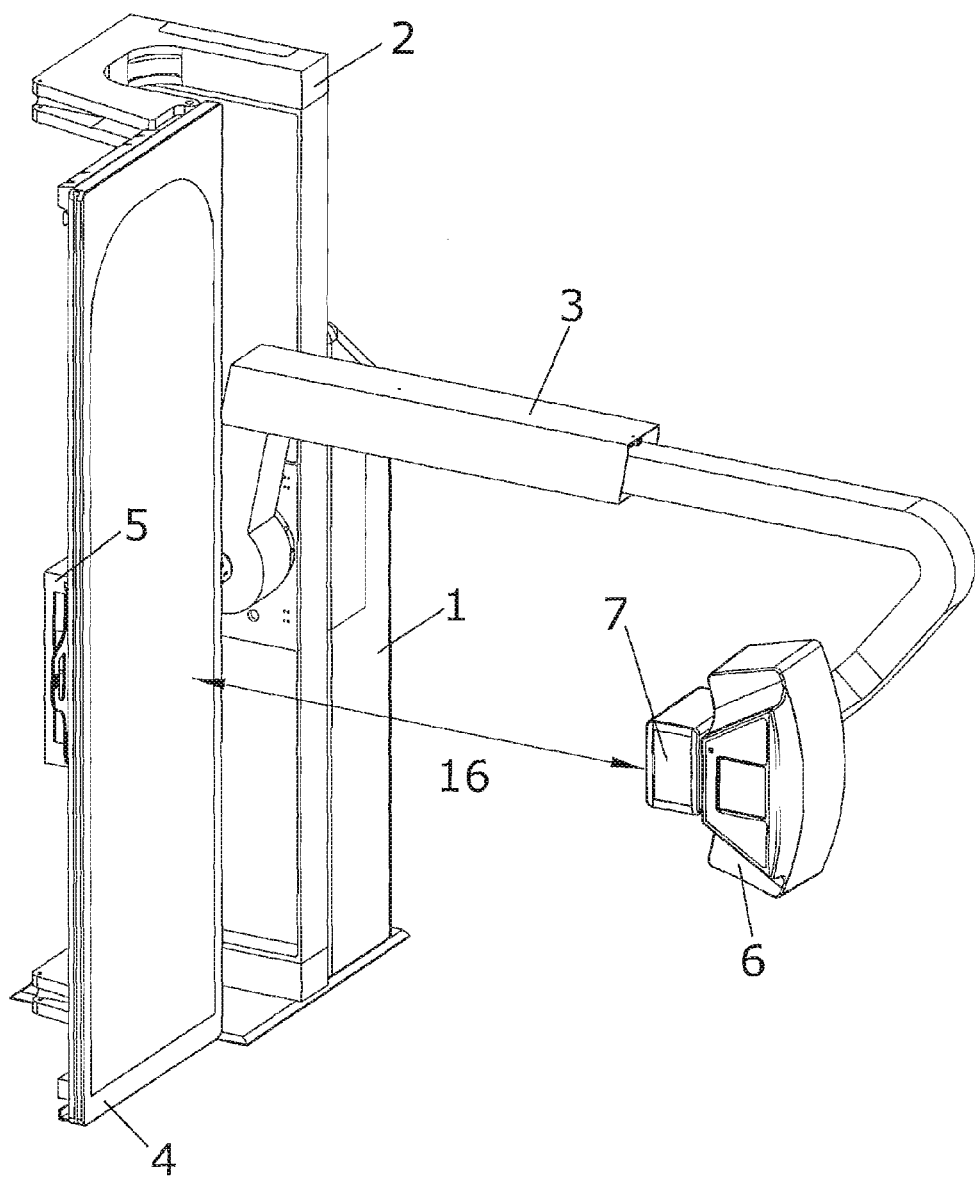
FIG. 5 shows a perspective view in which the assembly of the base and the elements joined to it has been turned 90° with respect to the fixed control and power supply column.

In addition, the revolving base (2) assembly can rotate (9) about a horizontal axis with respect to the fixed column (1), turning the entire revolving base (2) assembly and the elements connected to it, as can be seen in FIG. 5.

On another hand, when the attachment of the support plate (17) to the revolving base (2) is released, the support plate and its associated elements, this is, the arm (3) and the detector (5), can move longitudinally (10) along the revolving base (2).

Mounted on the support plate (17) are the arm (3) of the x-ray and collimator assembly, as well as the detector, the arm (3) being may rotate (11) with respect to the support plate (17) independently of the detector (5). The rotation (11) of the arm (3) allows performing tomosynthesis.

The arm (3) can also move the x-ray tube and collimator assembly along a vertical longitudinal sense (12).

Finally, the folding board (4) has a displacement movement (13) towards or away from the revolving base (2) as well as a rotation (14) with respect to hinges provided on its ends, which allows folding the board (4) so that it can be parallel to the revolving base (2).

Figure 3:
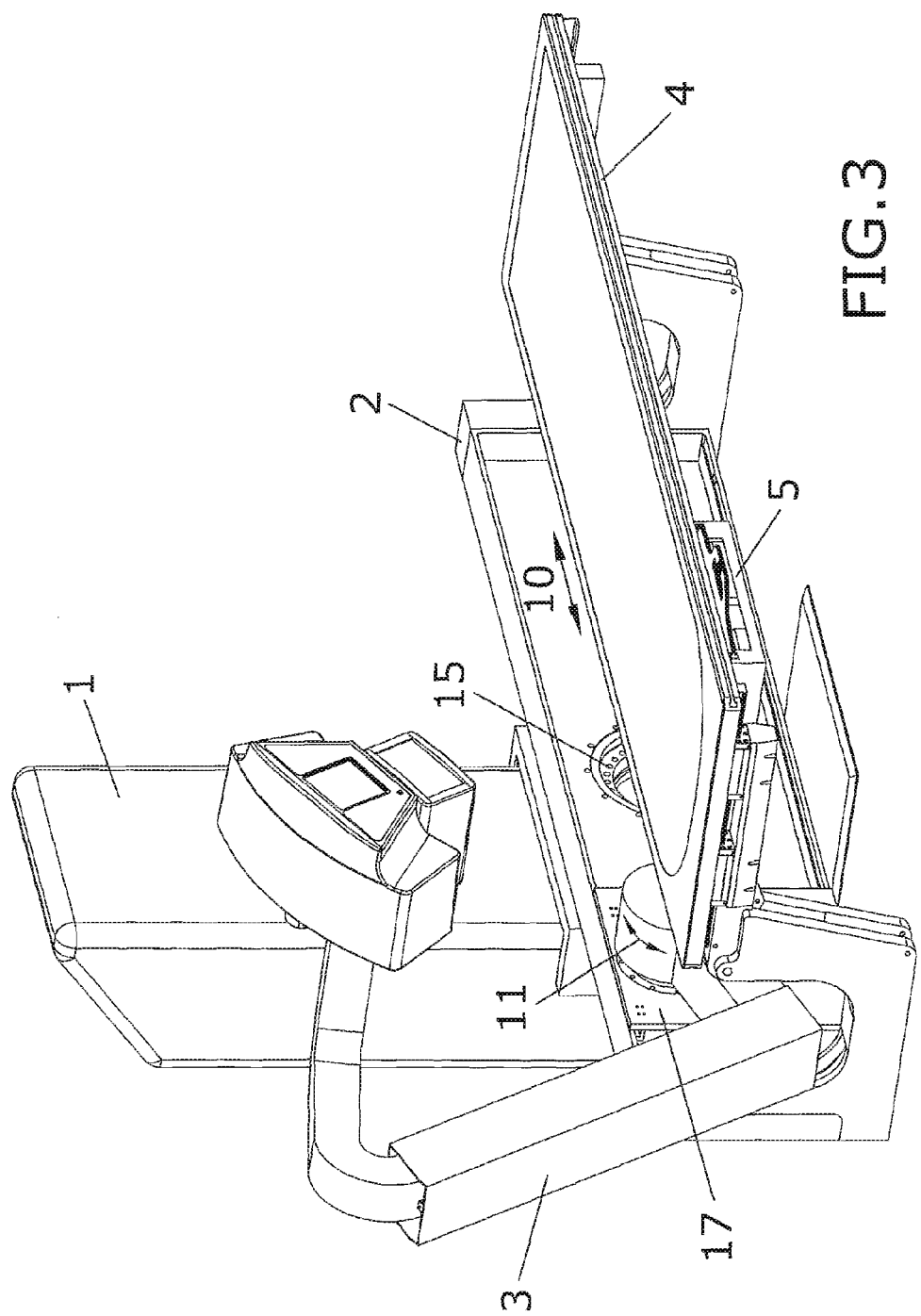
FIG. 3 shows a perspective view of the x-ray apparatus showing the rotation of the arm of the x-ray tube and collimator assembly independently of the revolving base.

FIG. 3 shows how the support plate (17) is released from its attachment to revolving base (2) and is longitudinally displaced revealing the orifice (15) of the revolving base. The support plate (17) now has a degree of freedom as it can move in a longitudinal sense (10) along the revolving base (2). It must be noted that the arm (3) can turn independently of the detector (5), thereby allowing tomosynthesis to be performed.

The attachment/release of the support plate (17) with respect to the revolving base (2) is performed by anchoring and release means disposed on the top and bottom edges of the support plate (17).

Figure 4:
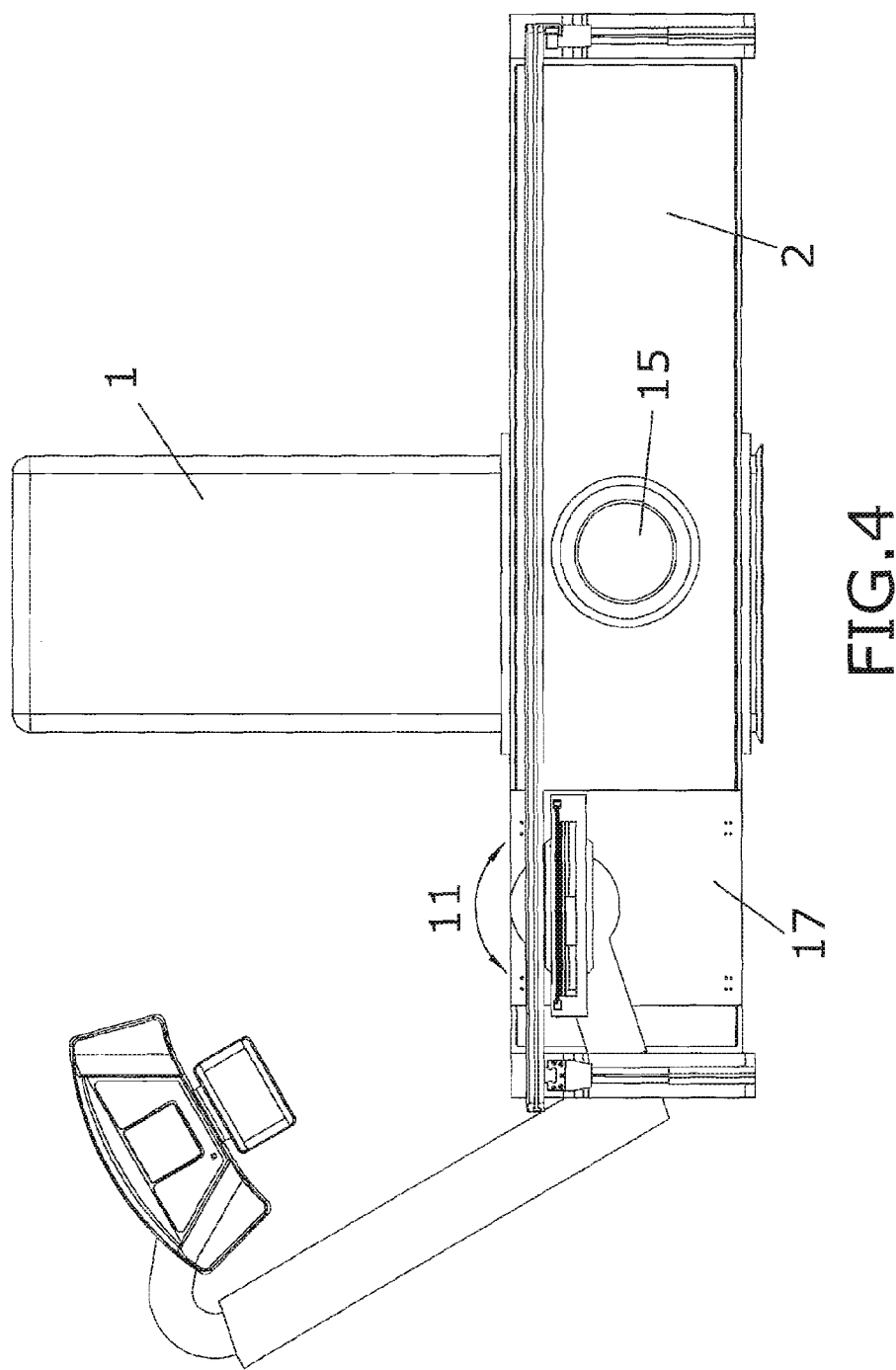
FIG. 4 shows a front view of the aforementioned assembly.

The front view of FIG. 4 shows the orifice (15) for connecting the support plate (817) to the fixed column (1), which constitutes the axis with respect to which turns the revolving base (2). Note that this orifice is disposed near one of the sides of the fixed column (1).

The proximity of the orifice (15) and the rotation axis to one of the sides of the fixed column (15) means that when the revolving base (2) assembly turns with all of the elements attached to it, they are placed to one side of the fixed column (1) so that between the x-ray tube (6) and collimator (7) assembly and the folding board (4) there is a distance (16), as shown in FIG. 5. This distance (16) is uninterrupted in its entire length and large enough to allow a stretcher to pass, thereby allowing to obtain a lateral radiograph of a patient without having to move the patient from the stretcher on which he/she has been brought.

The essence of this invention is not affected by variations in the materials, shape, size and arrangement of its component elements, described in a non-limiting manner, which should allow its reproduction by an expert in the field.

The invention claimed is:

1. An x-ray apparatus comprising:
   a fixed column (1) for control and power supply;
   a revolving base (2) mounted on the fixed column (1) and movable vertically (8) along the fixed column (1) and turnable (9) about a horizontal axis with respect to the fixed column (1);
   a folding board (4) that is connected to the revolving base (2);
   a support plate (17) mounted on the revolving base and partially releasable from its attachment to said revolving base (2) so that it has a degree of freedom and is movable longitudinally (10) along a length of said revolving base (2) by means of two guides provided in the revolving base (2);
   a detector (5) and an arm (3) on which is disposed a x-ray tube (6) and collimator (7) assembly both of them mounted on said support plate (17), and
   the arm (3) being U-shaped and movable along a longitudinal sense to be raised and lowered with respect to the board (4) and turnable (11) with respect to the support plate (17) independently of the detector (5).

2. An x-ray apparatus according to claim 1, wherein the attachment of the support plate (17) to the revolving base (2) is performed with anchoring and release means disposed on the top and bottom edges of the support plate (17).

3. An x-ray apparatus according to claim 1, wherein the folding board (4) has a movement (13) towards or away the revolving base (2), as well as a rotation (14) that allows folding the board (4).

* * * * *